(12) United States Patent
Holley

(10) Patent No.: US 6,388,751 B1
(45) Date of Patent: *May 14, 2002

(54) APPARATUS FOR DETERMINING OPTICAL PROPERTIES OF LIQUID SAMPLES

(76) Inventor: John Ernest Foster Holley, 9 Ship Field Close, Tatsfield, Westerham, Kent, TN16 2AU (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,436
(22) PCT Filed: Sep. 11, 1997
(86) PCT No.: PCT/GB97/02437
  § 371 Date: Jun. 9, 1999
  § 102(e) Date: Jun. 9, 1999
(87) PCT Pub. No.: WO98/11423
  PCT Pub. Date: Mar. 19, 1998

(30) Foreign Application Priority Data

Sep. 11, 1996 (GB) .............................................. 9618923

(51) Int. Cl.[7] .............................................. G01N 21/25
(52) U.S. Cl. ..................... 356/436; 356/440; 422/82.09
(58) Field of Search ................................ 356/436, 440; 422/82.09

(56) References Cited

U.S. PATENT DOCUMENTS

| 3,544,225 A | * | 12/1970 | Wattenburg | 356/436 |
|---|---|---|---|---|
| 3,770,382 A | * | 11/1973 | Carter et al. | 356/246 |
| 3,897,216 A | * | 7/1975 | Jones | 356/246 |
| 4,358,203 A | * | 11/1982 | Citrin | 356/432 |
| 4,729,661 A | * | 3/1988 | Bell | 356/437 |
| 4,810,096 A | * | 3/1989 | Russell et al. | 356/436 |
| 5,059,025 A | * | 10/1991 | Ando | 356/440 |
| 5,784,152 A | * | 7/1998 | Heffelfinger et al. | 356/436 |

FOREIGN PATENT DOCUMENTS

| DE | 41 17 008 A1 | 11/1991 |
|---|---|---|
| EP | 0 023 337 A1 | 2/1981 |
| EP | 0 068 717 A2 | 1/1983 |
| EP | 0 245 290 A2 | 11/1987 |

* cited by examiner

Primary Examiner—Richard A. Rosenberger
(74) Attorney, Agent, or Firm—Connolly Bove Lodge & Hutz LLP

(57) ABSTRACT

An apparatus for measuring optical characteristics of liquid samples, clinical samples for example, has an optical head (21) which is adapted to scan past a rack (12) of sample containers first in one direction and then in the opposite. The optical head has reference and test light sources (22) and corresponding light detectors (28) and separate optical paths are provided in the head for developing reference and test beams passing through the scanned samples. A fixed band pass filter is provided in the reference path and a filter wheel with a plurality of different band pass filters is provided in the test path, the apparatus being arranged to index the requisite filter into the test path in dependence upon the results of the reference scan. The optical head is driven by a reversible stepper motor (26) via a toothed drive belt (27) and this enables the output signals from the detectors to be correlated to the specific samples in the rack.

15 Claims, 7 Drawing Sheets

APPARATUS FOR DETERMINING OPTICAL PROPERTIES OF LIQUID SAMPLES

FIELD OF THE INVENTION

The present invention relates to an apparatus for determining optical properties of liquid samples. More particularly, but not exclusively, the invention relates to an apparatus for carrying out tests pertaining to chemical chemistry, enzyme immuno assays (EIA), enzyme linked immunosorbent assays (ELISA) and turbidimetric assays for example.

BACKGROUND OF THE INVENTION

Various optical arrangements are known for measuring and analysing biological/chemical test samples. For example, conventional spectrophotometers are available commercially, but such instruments are typically bulky, not inexpensive and require a high degree of operator skill or specialisation. Various automated analysis systems of the kind described in U.S. Pat. No. 3,770,382 and U.S. Pat. No. 3,897,216 are also known, in which the sample cells are transported sequentially through a test station on a conveyor chain during the course of a test operation. Such systems are typically large and complex in design and are correspondingly expensive. Further, optical density measuring apparatuses of the kind described in U.S. Pat. No. 4,729,661 are known in which the specimens are contained within a cuvette tray and movement of the cuvette tray through a test station is effected by translating the tray along an open channel defined in and along the front edge of the chassis of the apparatus.

In the above-mentioned prior art devices, sample cells are passed sequentially through a beam of light and the light signal transmitted therethrough is then detected and processed. Typically the sample cells are in the form of expensive microcuvettes having optical quality faces to ensure that test results are not degraded by imperfections in the sample containers. The prior art devices also commonly have had to employ a number of light sources to ensure that a sufficiently high level of light intensity is produced over a broad spectral band of wavelengths. For example, special-design light bulbs have had to be employed to perform measurements in the ultraviolet waveband. In the known devices, it is also difficult to position or locate accurately the sample(s) with respect to the light beam which adds an unwanted uncertainty to each measurement.

The aim of the present invention is to provide an improved apparatus which overcomes or substantially reduces at least some of the above-discussed drawbacks and limitations.

SUMMARY OF THE INVENTION

According to the present invention there is provided an apparatus for determining optical properties of liquid samples held in transparent containers, said apparatus comprising:

means defining a mounting for a plurality of said containers in a linear array;

an optical head mounted for translation along the length of said array, said optical head including a light source on one side of the array, a light detector on the other side of the array for detecting light from the source after it has passed through the array, and means defining an optical path between the source and the detector such that in use of the apparatus the light from the source scans across the liquid samples as the head is moved; and means responsive to the output of said light detector during translation of the head along the length of the array for determining the optical properties of each of the samples in the array.

A housing of the apparatus is advantageously provided with an opening at its upper surface for receiving a carrier which defines the mounting for the containers in the linear array. The array may be in the form of a rectilinear array, and the optical head may be arranged so as to move rectilinearly.

The housing of the apparatus and the carrier may be configured so as to inhibit the passage of extraneous light through the housing opening when the carrier is inserted.

Further, the optical head may be mounted on a carriage, or alternatively, the optical head may comprise a carriage. The carriage is, advantageously, engaged with one or more guide rails in the apparatus to permit movement of the optical head/carriage along the length of the rails. The carriage may also comprise linear bearing means which ensures easy movement of the optical head/carriage along the rail(s). Advantageously, the carriage includes spaced-apart wheels adapted to run on a support track provided in the apparatus. The wheels may be configured so as to produce a (sufficient) reaction force which biases the carriage into firm contact with the rail(s).

Furthermore, the apparatus may include an electric drive motor coupled to the carriage by means of a drive belt. The electric drive motor is preferably in the form of a reversible stepper motor. The drive belt is preferably in the form of a toothed belt. Such an arrangement enables a controlled movement of the optical head past the array of samples and also enables a corresponding controlled analysis of the output of the light detector for each sample.

The apparatus may provide means for supplying pulsatory drive signals to the drive motor and means for correlating the output of the detector with the positions of the samples in the array.

The apparatus may provide processor means for controlling the application of drive signals to the motor and for effecting sampling of the detector output, thereby identifying in the detector output that signal portion which corresponds to each of the samples. The processing means may also be arranged to effect a curve fitting algorithm upon the signal portions associated with the separate samples. Such a curve fitting algorithm may be structured to take no account of glitches in the signal portions corresponding to imperfections in the containers. In addition, the processing means may be arranged to derive a weighted average of the signal portions associated with the samples. This kind of processing advantageously enables high precision, reproducible measurements to be made on test samples contained in simple test tubes as opposed to in expensive microcuvettes.

The optical head may preferably comprise a solid block (for example, made of aluminium alloy) defining a mounting for the light source, a mounting for the light detector and a recess for the passage of containers through the optical head when the head is moved during operation of the apparatus. The provision of such a block head limits unwanted aberrations in the optical path and inhibits the passage of extraneous light through the apparatus. Further, the provision of a moving head past the samples permits the apparatus to be in a compact, portable form. The apparatus may, for example, fit into a briefcase.

Advantageously, the optical head may include a filter carrier (for example, a filter wheel system) having a plurality of different bandpass or interference filters mounted therein. The apparatus may also be adapted and arranged to introduce automatically the requisite filter into the optical path.

Preferably, the apparatus may include a bar code reader for entering information into the apparatus so as to condition the apparatus for the performance of specific optical property tests.

The apparatus may further include means for adjusting the power supplied to the or each said light source so as to determine the optimum spectral output and/or the intensity thereof. Standard tungsten-halogen bulbs with a quartz envelope may, for example, be employed to perform measurements in the ultraviolet waveband.

The apparatus may be used to carry out numerous routine and speciality laboratory tests quickly and to a high precision. Use of the apparatus does not require a high degree of operator skill or specialisation. The apparatus may be mains-operated or operated from batteries.

The above and further features of the present invention are set forth in the appended claims and, together with advantages thereof, will become more clear from consideration of the following detailed description of exemplary embodiments of the invention given with reference to the accompanying drawings.

DETAILED DESCRIPTION OF THE EMBODIMENTS INVENTION

Figure 1:
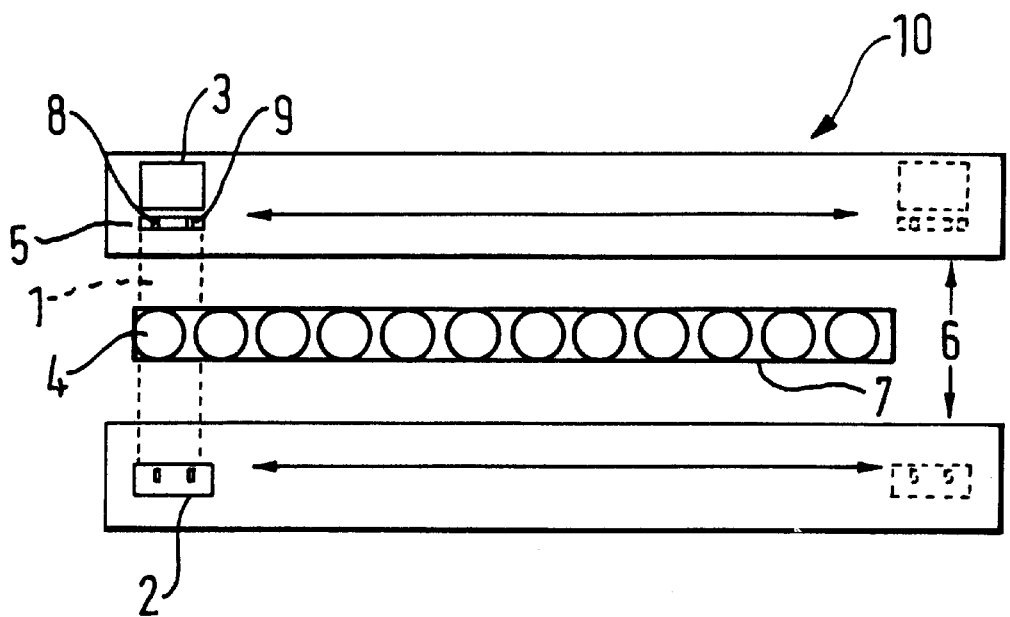
FIG. 1 shows a schematic plan view of an exemplary apparatus embodying the present invention.
Figure 2:
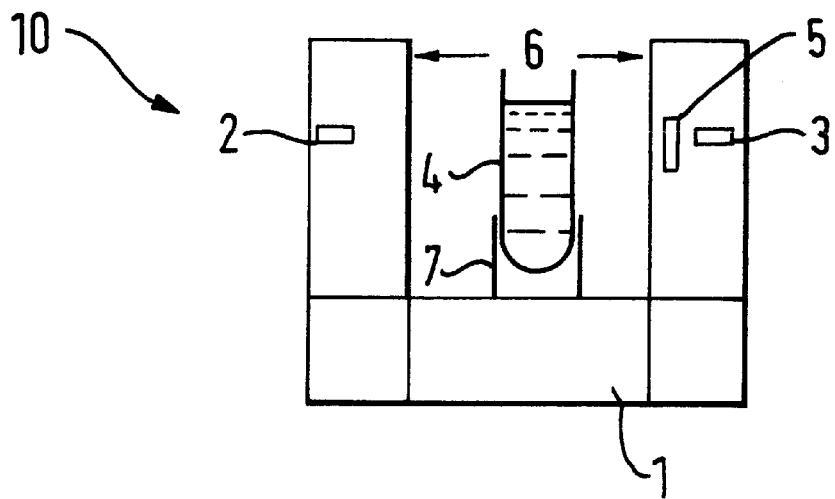
FIG. 2 shows a schematic and elevation view of the apparatus of FIG. 1.

The embodiment of FIGS. 1 and 2 is only schematically illustrated and will be discussed in general terms hereinafter before a particular and detailed description is provided of the embodiment of FIGS. 3 to 7. In the embodiment of FIGS. 1 and 2, the samples are preferably held in transparent containers arranged in a linear array. The light emitter and light detector are mounted on a track with the light emitter on one side of the array and the light detector on the other side of the array with the emitter and detector aligned appropriately. The emitter and detector can move past the transparent containers in both directions. The emitter and detector are mounted with a gap between them into which transparent containers can be placed, for example the transparent containers can be mounted in a pre-loaded cassette which fits in the equipment, so that transparent containers can be easily replaced.

In order for different wavelengths of light to be used, there is a means to enable a filter to be positioned in the light beams from the emitter either before or after it passes through the transparent containers. There are means to change the filter so that different filters can be used for different transparent containers. The filters are bandpass or interference filters which pass a selected spectrum or wavelengths of light.

There are two light emitters and corresponding detectors positioned to pass light through the transparent containers with one light source being used as a reference and the other light being used to detect the difference in absorption or reflectance at a second wavelength or spectrum of wavelengths.

In order to avoid errors due to the difference in intensity of the light from two independent light sources, a transparent container containing liquid of known absorption can be used to obtain a measurement from both light sources and the microprocessor and regulator can then automatically make any adjustment required to obviate any difference in the intensity of the light from the different light sources.

This ability is also used to help increase the life of the lamps used as the light source, by causing the power into the lamp to be changed as the output grows dimmer, therefor bringing the light output back to the required level.

In word, the wavelength of the light can be chosen by choice of different filters, so that a particular reagent or compound can be detected, making it possible, with the same liquid in each transparent container, to detect more than one reagent or compound. The output from the detector can be fed into a computer for processing, e.g so that a printed output can be obtained. The same compound can be used to control the operation of the emitter and detector and other components.

Preferably, there is a light emitter which emits light which passes through two side by side filters, the first of which transmits light of a frequency which is substantially not affected (e.g. absorbed or reflected) by the reagents or compounds in the liquid in the transparent containers which are to be detected, measured or analysed and the second filter transmits light of a frequency which is so affected.

The light from the first filter passes through the liquid in the transparent containers or, preferably, passes through the filter after it has passed through the transparent container, and acts as standard or reference to measure the degree of absorption or reflectance of the liquid. The light from the second filter measure or detects the change in the reagents or compounds in the liquid. This arrangement substantially reduces zero errors etc. and gives a measure of the difference of absorption or reflectance at the two spectrum bandwidths corresponding to the light passing through the filters.

There can be a means to change the second filter in a preselected manner so that a particular filter can be used at a particularly transparent container, this can be done for example by a switch moving a carousel on which are mounted a series of different filters; the switch can operate at one end of the movement of light emitters and detectors along the track.

Preferably when the light source and its corresponding detector passes down the track in one direction the reference light source is operational and when it passes back down in the opposite direction back to the start position the other light source is operational.

In order to measure a property such as the optical density of a liquid in a transparent container, a series of readings can be taken as the light source passes across each transparent container, with the light intensity measured by the detector. By the use of a microprocessor the average optical density for each sample in each transparent container can be obtained. Preferably, the movements of the emitter and detector are operated by a stepper motor so that the speed past each transparent container can be controlled.

By use of microprocessor control and filter changes, it is possible to have a preselected filter used for any particular transparent container; preferably, the operation of the equipment is controlled by a microprocessor so that the equipment will run automatically and the results obtained as readings or a print out etc. in the desired form.

When two independent light sources are used one source can be an ultraviolet emitter which will then also enable the system to operate as a fluorescence detector.

Referring now to FIGS. 1 and 2, there are shown therein in schematic plan and end elevation views the essential component parts of an apparatus embodying the invention. The apparatus generally indicated at (10) includes a track (1) having light emitters (2) and light detectors (3) mounted on it so they can be moved as shown in FIG. 1. Transparent containers (4) can be placed in a cassette (7) which fits in the gap (6). During a scan, light emitted from the light emitters (2) passes through each of the transparent containers (4), through filters (8) and (9) mounted in filter holding means (5) into the light detectors (3). The filter (9) can be changed so that different wavelengths of light can be used.

The filter (8) passes light of a wavelength substantially unaffected by the reagents or compounds which are to be detected, so that it provides a reference signal, and the filter (9) is chosen in accordance with the reagent or compound to be detected and the difference in the signals is a measure of this reagent or compound.

In use, the transparent containers (4) containing the liquid whose optical properties are to be determined are placed in cassette (7) in position in the equipment. One of the light emitters (2) is turned on and acts as a reference and the light passes through filter (8), as shown. The emitters (2) and detectors (3) are connected to a movable track (1) together and automatically aligned. The emitters (2), filter holder (5) and detectors (3) move sequentially past the transparent containers (4) down the track in one direction and the light passing through them is detected by the detectors to enable optical properties at the spectrum of filter (8) to be determined. When the end of the track is reached the other light source is then turned on and the light passes through container (4) and filter (9) and the emitter and detector then pass down the track (1) in the opposite direction and the optical properties are determined from the spectrum of filter (9).

There are a series of filters (9) in the filter holder (5) to enable different spectra of wavelengths to be used for the transparent containers. When the emitter reaches the end of the track, and before it is reversed, the filter (9) can be preselected.

The movement of the light emitters (2) and light detection (3) along the track, and the operation of the apparatus is controlled by a microprocessor which can automatically process the signals, compare the results at the different spectra of wavelengths and print out the results in the desired form.

Figure 3:
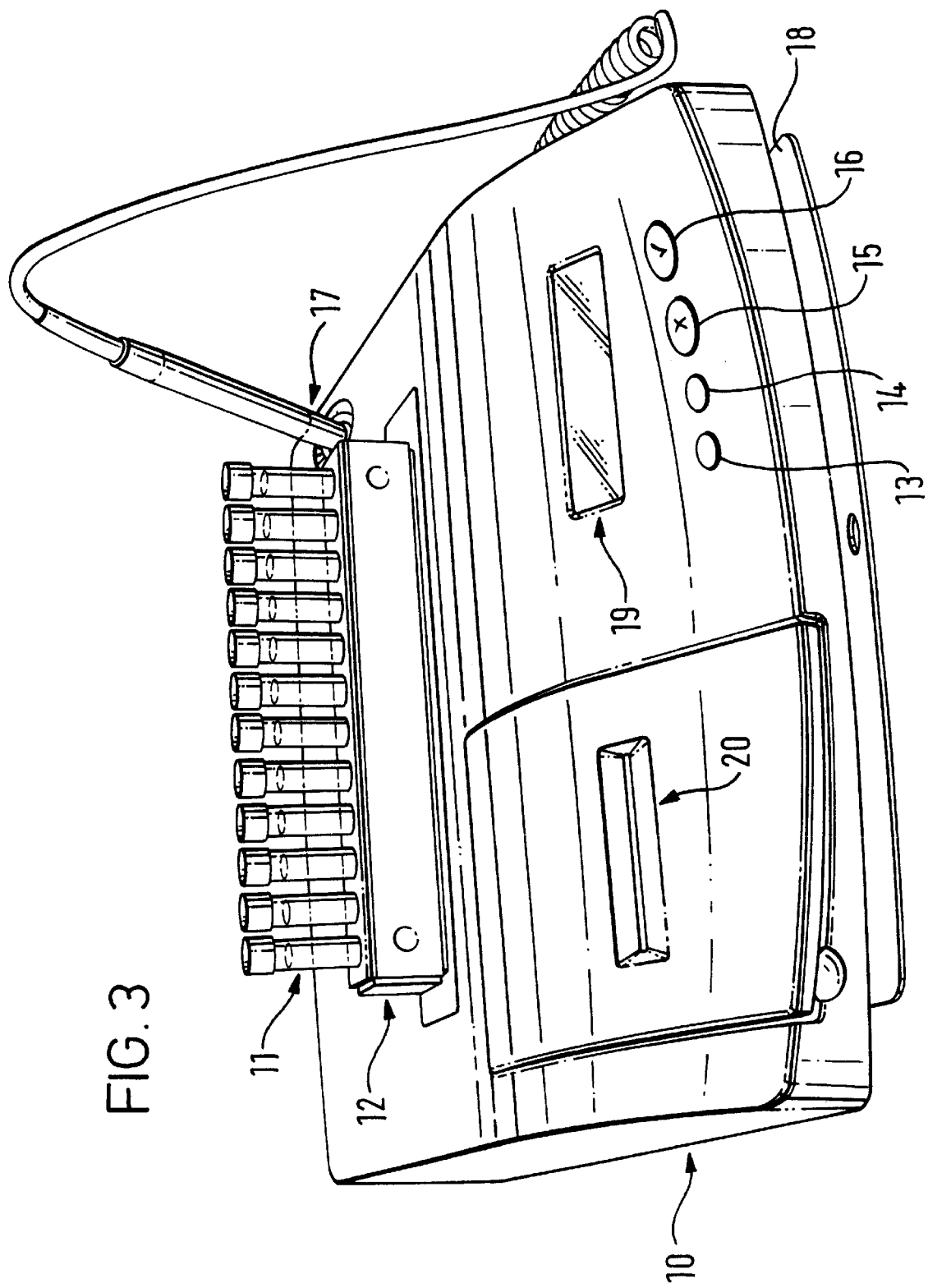
FIG. 3 shows a perspective view of the external appearance of another apparatus embodying the invention.

Referring next to FIG. 3, there is shown therein a perspective view of the external appearance of an actual apparatus (10) embodying the invention. As shown in the figure, the apparatus may be provided with a cassette or rack (12) into which up to twelve test tubes or microwells (11) may be loaded. Cassette (12) is suitably dimensioned for insertion into the apparatus (10). All information concerning the optical property tests and the corresponding mathematical reductions required to carry out such tests may be input by optical barcode (18) by use of a light pen (17). Each of the test tubes or wells may be read up to 3,000 times thereby rendering exceptional reproducibility during the course of measurement and the results can then be averaged and printed out on a printer. In addition, the results can be downloaded onto a personal computer by virtue of the provision of an RS232 port in the apparatus. The apparatus (10) as shown is portable and fits into a briefcase. Its dimensions are typically 365×310×50 mms and has a weight of less than 2 kgs. As part of the user interface, there are two main buttons (15,16) corresponding to "no" and "yes" and two other buttons (13,14) corresponding to "scroll up" and "scroll down". The apparatus also has a slot (20) for feeding printer paper therethrough.

A person wishing to perform a test scan by use of the apparatus (10) must carry out a series of operations in a specific order namely:

first switching the apparatus on which causes a visual display (19) to ask for information so as to condition the apparatus for the performance of the test, then scribing in information using the barcode reader and pen (17,18) or with a keyboard coupled to the RS232 port, inserting the cassette (12) of test tubes (11) into the apparatus and pressing the "yes" button (16).

In the event that the wrong information is scribed in, the button "no" may be pressed.

Given that the "yes" button is pressed, the optical head of the apparatus (not shown in FIG. 3) proceeds to scan across each of the samples held in the cassette.

A discussion of the controlled scanning movement of the optical head past the array of samples will follow.

Figure 4:
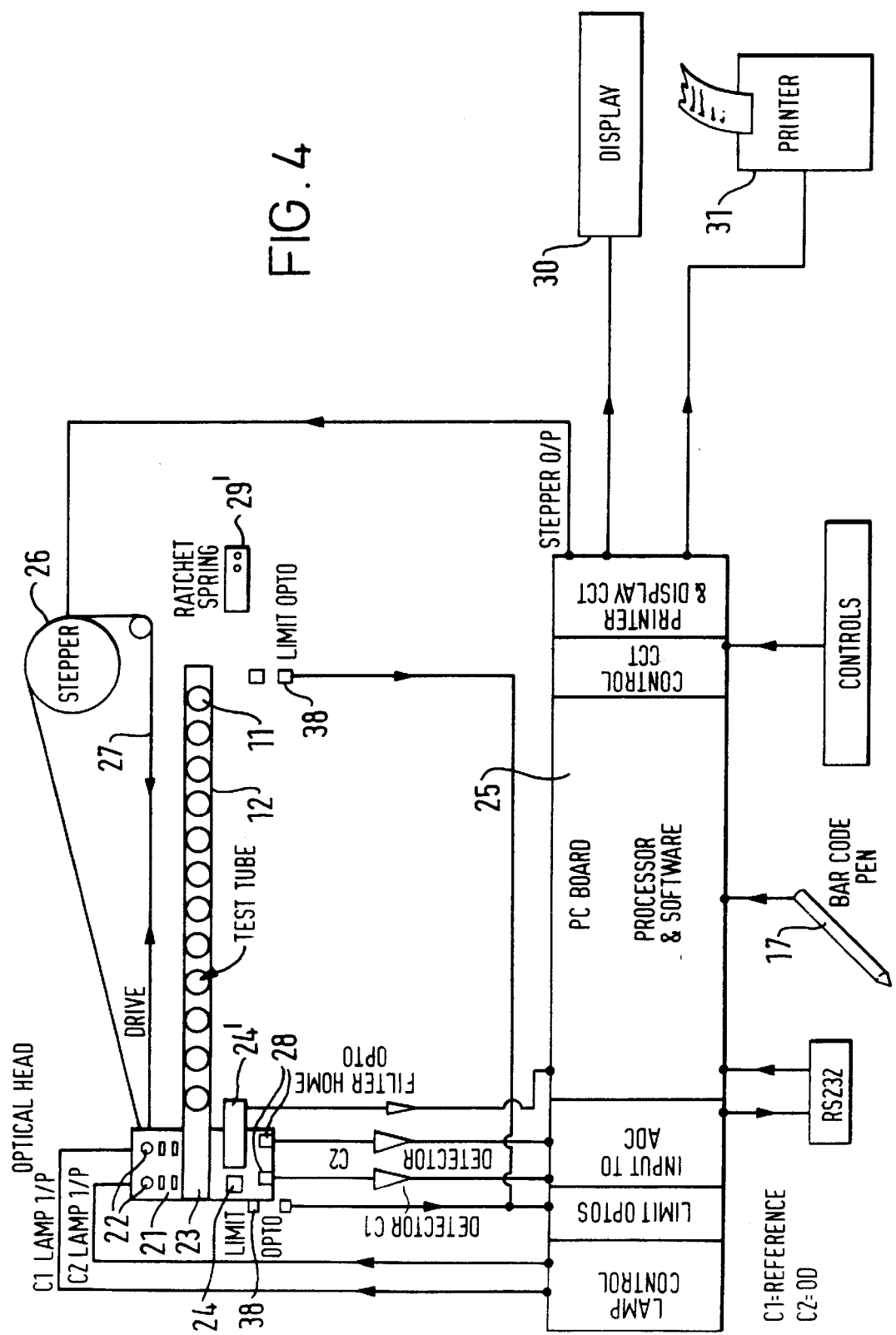
FIG. 4 shows a schematic block diagram view of the apparatus of FIG. 3.

FIG. 4 shows a schematic view of the assembly of component parts of the apparatus embodying the invention. The apparatus comprises an optical head (21), preferably in the form of a solid block made of aluminium alloy, which is mounted for translation along the length of the plurality of containers (11) arranged in linear array, the optical head further defining a mounting (22) for the light sources, a mounting (28) for the light detectors, and a recess (23) for the passage of containers (11) through the optical head (21) when the head is moved during operation of the apparatus. It is to be noted that light emitted by the light source is channelled through the block head (21) thereby defining the optical path and intercepting the recess (23). As shown in this figure the solid block (21) comprises mountings for separate test and reference light detectors (28) and separate channels are provided through said block to define said separate test and reference channels.

FIG. 4 shows the interaction between the optical head component part and the stepper motor and the processor/software unit. As shown, the apparatus comprises a reversible stepper motor (26) coupled to the optical head (21) by means of a drive belt (27). The drive belt (27) is envisaged to be a toothed belt and the arrangement is such that it enables a controlled movement of the optical head (21) past the array of samples in the containers (11) and a corresponding controlled analysis of the output of the light detector for each sample. As shown, the apparatus may also comprise means for supplying pulsatory drive signals to the stepper motor and for correlating the output of the detector with the positions of the samples in the array. It is to be noted that the processing unit which is preferably in the form of microprocessor (25) may be used to control the application of drive signals to the motor and correspondingly to effect sampling of the detector output so as to identify in the detector output that signal portion which corresponds to each of the samples. The processing unit (25) is arranged to effect a curve fitting algorithm upon signal portions associated with the separate samples. Furthermore the curved fitting algorithm is structured to take no account of glitches in signal portions corresponding to imperfections in the containers (11). The microprocessor may be arranged further to derive a weighted average of the signal portions associated with respective samples, the weighting being effected in consideration of the cross-section or shapes of the containers.

During the course of a scanning measurement, the microprocessor based controlled system (25) is adapted and arranged such that the optical properties of the samples are determined by first effecting a reference scan of the samples by translation of the optical head (21) along the length of the linear array and then effecting a test scan in the opposite direction by way of a further translation of the head along the length of the array. In this regard, according to the information scribed in by the barcode pen (17), selection of a reference filter and of an appropriate optical filter for the test scan may be automatically effected by the apparatus. In FIG. 4, the appropriate filters (reference and test) are introduced into the optical path at positions 24,24' as defined in the optical head (21). The optical head (21) includes a filter carrier in the form of an indexable filter wheel having a variety of different bandpass or interference filters mounted therein and which wheel is arranged to co-operate with abutment means (29) at one end of the range of movement of the optical head (21) for indexing the wheel by one position. Such an arrangement enables the filter wheel to be indexed to any desired position by controlled reciprocation of the optical head at said one end of its range of scan movement.

It is to noted that the processor/software unit (25) samples and converts the output analogue signal of the light detectors into a digital form and, inter alia, smooths and averages and combines the digital data in a weighted fashion so as to enable optical properties of the samples to be determined. Typically, the smoothed/averaged reference scan data are subtracted away from the smoothed/averaged test scan data to eliminate unwanted intrinsic effects of the instrumental response (such as noise). Furthermore, the unit (25) includes means for adjusting the power supplied to each said light source to determine the spectral output and/or the intensity thereof. The apparatus further includes a printer (31) and/or visual display (30) together with an RS232 port via which results can be downloaded onto a personal computer.

Figure 5:
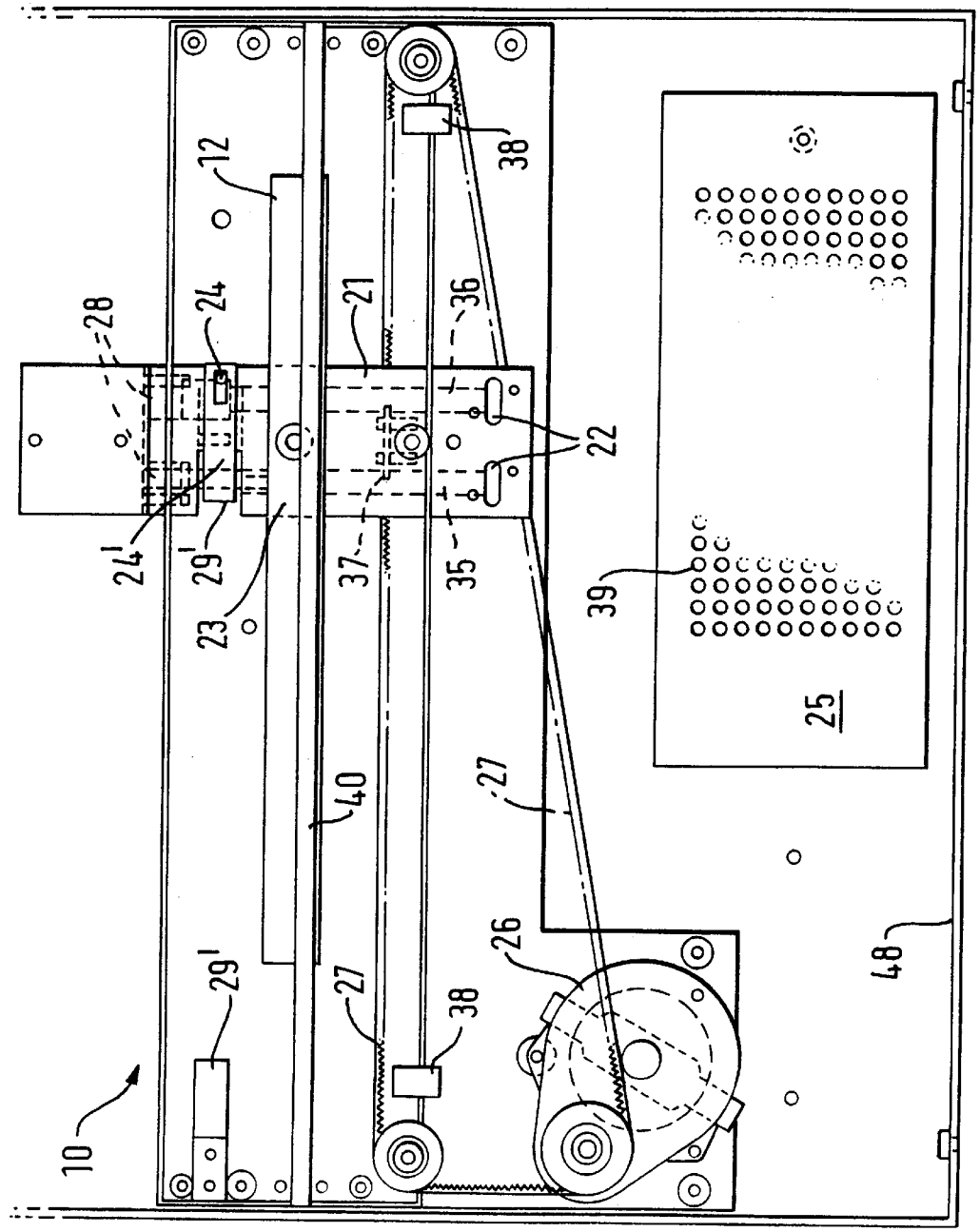
FIGS. 5 to 7 are views showing in more detail the component parts of the apparatus of FIGS. 3 and 4, FIG. 5 showing the apparatus in top plan view, and FIGS. 6 and 7 showing the same apparatus in front elevation and side elevation views.
Figure 6:
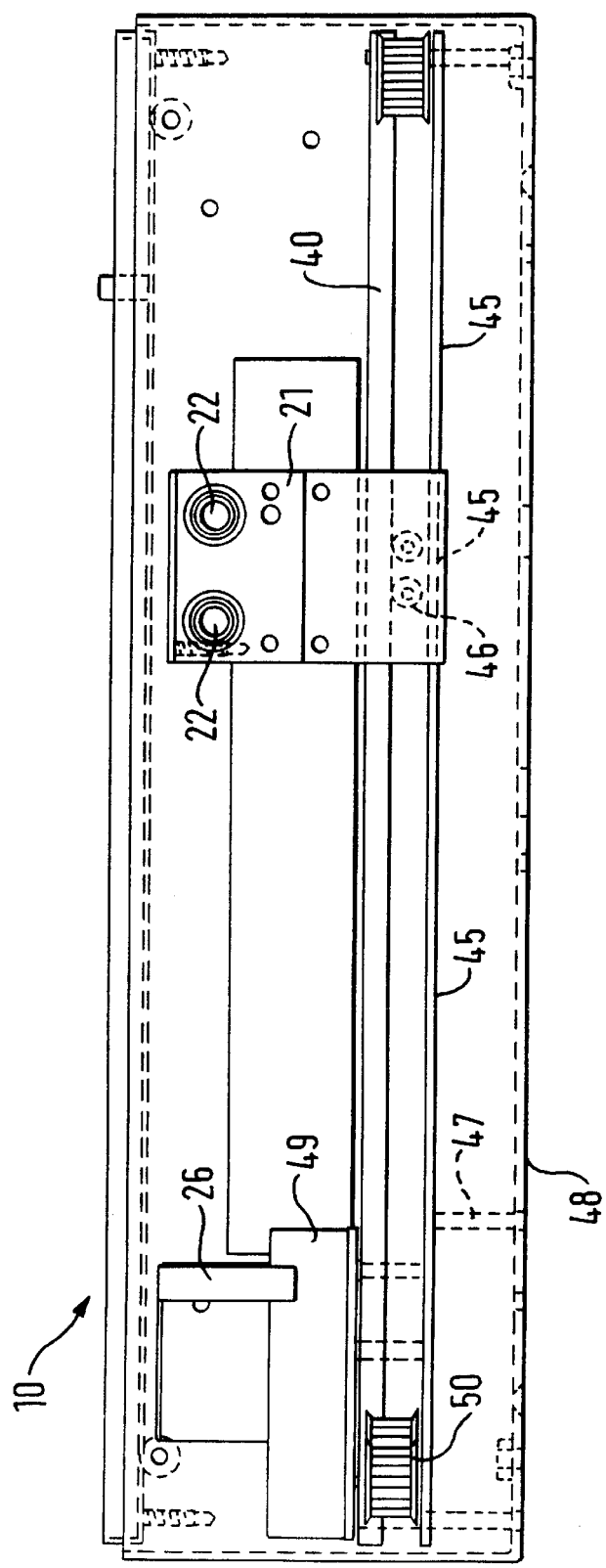
Figure 7:
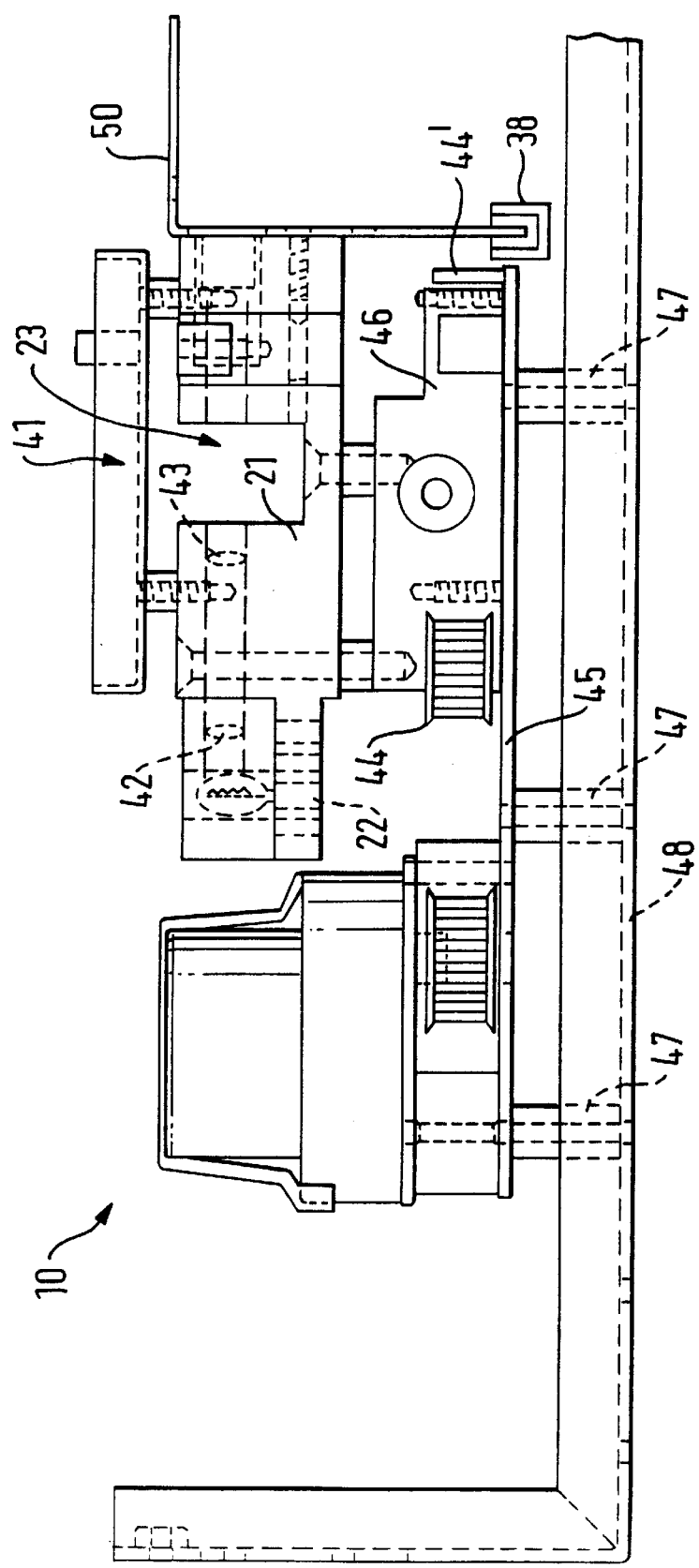

Finally, FIGS. 5 to 7 show in more detail the same component parts of the apparatus embodying the invention in top plan, front elevation and side elevation views. The Figures again use the same reference numerals as were used to designate same/like parts in the description of the previous Figures.

FIG. 5 shows the construction of the optical head (21), in further detail, and its interaction with other parts of the apparatus embodying the invention in top plan view. The head (21) in the form of a solid block is shown to have mountings for separate test and reference light sources (22), mountings (28) for separates test and reference light detectors and separate channels (35,36) provided through said block (21) so as to define separate test and reference channels (35,36). In such an arrangement, the reference scan is effected by use of the reference channel (36).

The block head (21) includes a recess portion (23) for the passage of containers which hold samples therein as the head is moved along the length of a guide rail (40) of the apparatus. The block head (21) also defines a mounting for the reference and test filters (24,24'). Preferably, and indexable filter wheel for carrying a plurality of different bandpass or interference filters mounted therein can be mounted at position 24' in the block and a suitable reference filter can be mounted at position 24 in the block. The filter wheel may be arranged to co-operate with abutment means, for example, with a top and bottom ratchet spring (29,29'), at one end of the scanning head's range of movement, the arrangement being such that the filter wheel can be indexed to any desired position automatically by controlled reciprocation of the head at said one end of its range of movement.

The head's range of movement is defined by use of the stepper motor (26), a toothed belt (27) which is engaged with the head and by optical limiting switches (38,38') which serve to define the start and end positions of the scan across the linear array of samples. It is to be noted that the drive belt (27) is engaged with a slot (37) the optical head.

As shown, the back of the apparatus includes the electronics and software (25) and an air vent (39).

As regards selection of the spectral range of the light sources mounted at positions (22) in this arrangement, bandpass or interference filters are preferably used which typically have a bandwidth of 10 nanometers and which cover a waveband between 300 nanometers to 700 nanometers.

FIG. 6 shows the apparatus of FIG. 5 in front elevation view. The apparatus includes an external housing (48) enclosing the optical head arrangement (21), a guide rail (40) along which the head is adapted to move, and the stepper motor system (26). The separate parts of the motor (26) including the motor gearbox (49) and the motor drive spindle (50) are shown in the Figure. The optical head (21) is adapted to run on a support track (45) provided in the apparatus, the track being supported in the housing (48) by means of mounting pillars (47). The bottom end of the support track (45) in the apparatus is designed to coact with the optical limiting switches (not shown here). Further, the optical head (21) is shown to be mounted on a carriage portion (46) which is engaged with the guide rail (40) in the apparatus so as to be movable along the length of the rail.

FIG. 7 shows the same apparatus of FIGS. 5 and 6 in side elevation view. The carriage portion (46) is shown here in more detail and includes linear bearing means which ensures easy movement of the carriage along the guide rail (40). The carriage (46) includes spaced apart oversized wheels (44, 44') which are adapted to run on the support back (45) provided in the apparatus. The oversized wheels (44,44') are configured to provide a reaction force such as to bias the carriage into firm contact with the guide rail (40) of the apparatus. The optical head (21) is also shown to include a lens arrangement in which a pair of lenses (42,43) are provided in the channels of the block head for establishing substantially parallel light beams across the recess portion (23). A cover portion (41) is engageable with the upper surface of the optical head so as to cover the recess portion (23) and block extraneous light from entering through the housing opening. The light source mounted at position 22 of the head is preferably a tungsten halogen lamp with a quartz envelope. For sake of completeness FIG. 7 shows mounting means (50) for the electronics of the instrumentation. The bottom end of the support track (45) is also shown to coact with the slotted optical limiting switches (38) of the apparatus.

Figure 8A:
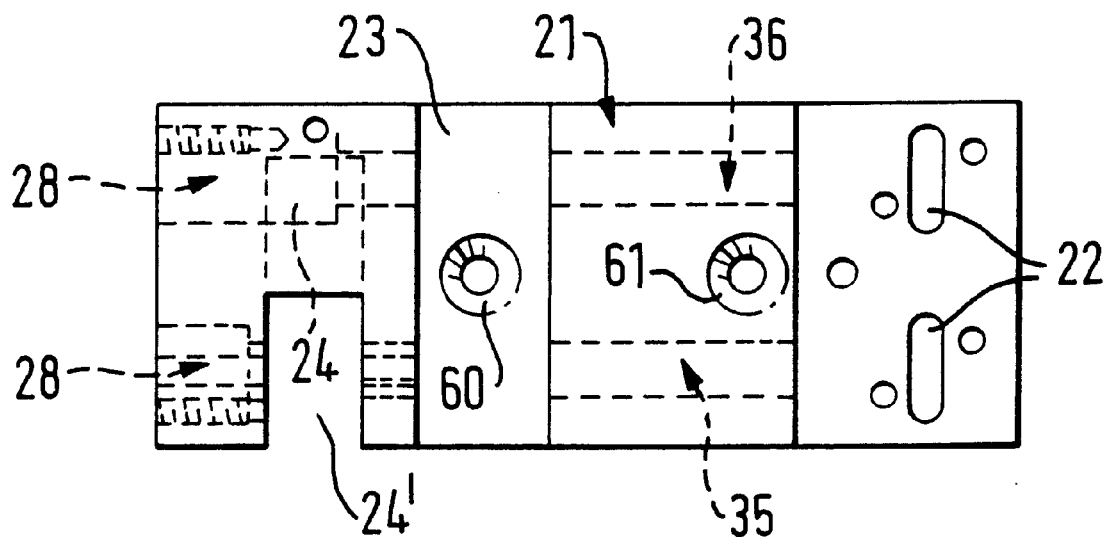
FIGS. 8($a$) to 8($b$) show the structure of the optical block head component in more detail.
Figure 8B:
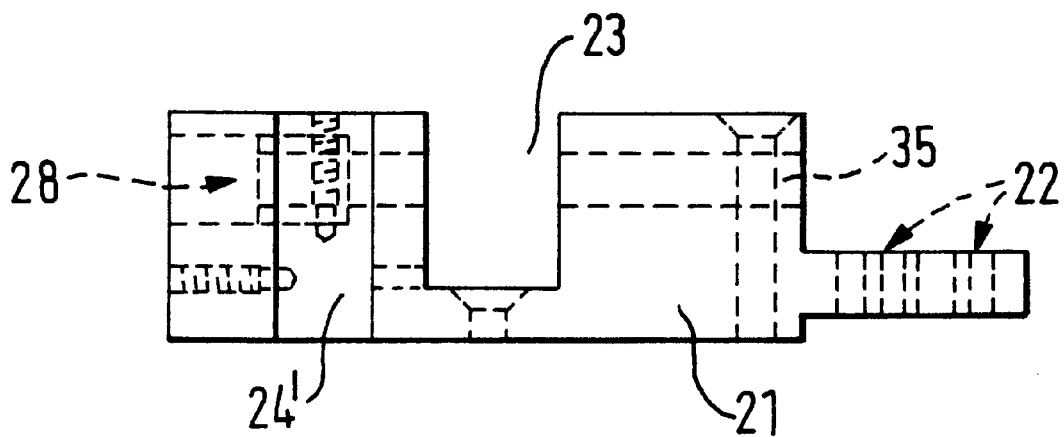

Finally, FIGS. 8(a) and 8(b) show the structure of the above-described optical block head (21), in more detail, in plan and side views. Typical block dimensions in millimeters are as shown. The block is preferably formed of aluminium alloy material. The figures again use the same reference numerals as were used to designate same/like parts in the description of FIGS. 4 to 7.

It should be noted from FIGS. 8(*a*) and 8(*b*) that the block head (21) has mountings for separate light sources (22), mounting for separate light detectors (28), a recess portion (23), and separate channels (35,36) running therethrough so as to define separate test and reference channels. During operation of the apparatus, the reference scan filter is inserted into position (24) of the block (21), and the filter wheel carrier which has a selection of optical filters mounted therein is inserted into position (24') of the block (21). The drilled holes (60,61) formed in the upper block surface are adapted to receive screws for attachment of a cover to the said upper block surface.

In operation of the machine of FIGS. 3 to 8 hereinabove described, the user switches on the machine and a display appears on the machine asking for information. The user can then scribe in information relevant to the test which is to be conducted by means of the bar code reader or by use of a keyboard connected to the RS232 port. A rack of test samples is then loaded into the slot in the top of the machine housing and the machine display then indicates an option to select "go" to initiate the test. The optical head of the machine then traverses the rack of samples from one side to the other and takes a reference reading of each tube, the reference light source being illuminated and the output of the reference detector being active. Having traversed the array of samples, the machine then selects the appropriate filter to be employed during the subsequent test scanning of the samples, this selection being effected in dependence upon the data entered into the machine by use of the bar code reader or other input device and in dependence upon the output of the reference detector during the reference scan of the optical head past the sample array. The selected filter is indexed into the optical path between the test lamp and the test detector by reciprocation of the optical head at the end of its reference travel. An optoelectronic detector ensures that the operating system "knows" the home position of the filter wheel and thus "knows" the whereabouts of each filter in the wheel.

Having selected the appropriate filter and introduced it into the light paths between the test light source and the test detector, the stepper motor is reversed so as to cause the optical head to scan back across the array of samples and the corresponding output of the test detector is processed.

The analogue outputs of the reference and test detectors are converted into digital signals with correlation with the stepper motor and drive belt position so that the machine "knows" which sections of the signals correspond to which samples. The digital signals are processed using a curve-fitting algorithm designed to discard aberrant signals (glitches) arising for example on account of scratches or other imperfections in the sample containers. A centre point is identified in the resultant curve for each sample and a weighted average is derived for each of the reference and test curves by sampling the curve at predetermined locations on each side of the centre point, the weighting being effected inter alia in dependence upon the cross-sectional shapes of the sample containers. Having derived weighted reference and test averages for each sample, these two averages are processed to obtain an indication of the optical characteristics of the samples, particularly their optical densities, and a corresponding record is provided on the printer or, via the RS232 port, to a computer monitor.

Having thus described the present invention by reference to exemplary embodiments, it is to be appreciated that modifications and variations thereto are possible without departure from the spirit and scope of the present invention. For example, a single channel or a plurality of channels may be provided through the optical block head so as to define the test and reference channels during the scanning process. In addition, whereas in the described exemplary embodiments the optical head is mounted on a separate carriage portion, the optical head/carriage can alternatively be of a kind comprising a integrally-formed unit.

What is claimed is:

1. An apparatus for determining optical properties of liquid samples held in transparent containers, said apparatus comprising:

a housing having an opening in an upper surface thereof for receiving a carrier which is adapted to receive a plurality of said containers in a rectilinear array, the arrangement being such that when the carrier is loaded with containers and is inserted into said opening liquid samples in the containers locate in predetermined positions within the housing;

an optical head mounted within said housing for rectilinear reciprocal translation along the length of said array, said optical head comprising a solid block having a recess therein which locates with said array and having a first portion on one side of the array and a second portion on the opposite side of the array;

at least one light source mounted on said first portion of said solid block and separate test and reference light detectors mounted on said second portion;

first and second light channels formed in said block between said at least one light source and said test and reference detectors, said channels intersecting said recess and being arranged such that in use of the apparatus a substantially parallel beam of light from said at least one source scans across the light samples as the optical head is moved and is received by said detectors after passage through the containers and the samples therein;

filter means comprising a plurality of individually selectable optical filters provided in the optical path to at least said test light detector;

an electric drive motor coupled to said optical head for effecting reciprocal movement thereof; and control means including data input means accessible to a user of the apparatus for enabling the operation of the apparatus to be predetermined in accordance with entered data, said control means being arranged to determine the operation of said motor and said filter means and to effect sampling of the light detector outputs to identify therein respective signal portions corresponding to each of the samples, said control means being arranged to determine the optical properties of the liquid samples by first effecting at least one reference scan by translation of said optical head along the length of the array and then effecting at least one test scan by further translation of the optical head along the length of the array.

2. An apparatus as claimed in claim 1 wherein housing of the apparatus and the carrier are so constructed and arranged as to inhibit the passage of light through the housing opening when the carrier is inserted.

3. An apparatus as claimed in claim 1 wherein the control means includes a microprocessor arranged to effect a curve fitting algorithm upon the signal portions associated with the separate samples.

4. An apparatus as claimed in claim 3 wherein the curve fitting algorithm is structured to take no account of glitches in the signal portions corresponding to imperfections in the containers.

5. An apparatus as claimed in claim 3 wherein the microprocessor is arranged to derive a weighted average of the signal portions associated with respective samples, the weighting being effected in consideration of the cross-sectional shapes of said containers.

6. An apparatus as claimed in claim 1 wherein said optical head includes a carrier having a plurality of different filters mounted therein, and the apparatus is adapted and arranged automatically to introduce the requisite optical filter into the optical path.

7. An apparatus as claimed in claim 6 wherein the carrier is an indexable filter wheel and means are provided in the apparatus for indexing the wheel to a relevant position.

8. An apparatus as claimed in claim 7 wherein said filter wheel is arranged to co-operate with abutment means at one end of the range of movement of the optical head for indexing the wheel by one position, the arrangement being such that the filter wheel can be indexed to any desired position by controlled reciprocation of the optical head at said one end of its range of movement.

9. An apparatus as claimed in claim 1 wherein lens means are provided in said channels for establishing substantially parallel light beams across said recess.

10. An apparatus as claimed in claim 1 wherein the solid block has separate test and reference light sources associated with said separate channels.

11. An apparatus as claimed in claim 1 wherein the control means includes a microprocessor arranged to process the outputs of the reference and test detectors separately and then to combine the results or the reference and test processes in determining the optical properties of the liquid samples.

12. An apparatus as claimed in claim 1 including means for adjusting the power supplied to each said light source to determine the spectral output and/or intensity thereof.

13. An apparatus as claimed in claim 1 including a bar code reader for entering information into the apparatus to condition the apparatus for the performance of specific optical property tests.

14. An apparatus as claimed in claim 1 including a printer and/or visual display.

15. An apparatus as claimed in claim 1 including a visual display.

* * * * *